United States Patent [19]

Ellebracht et al.

[11] 4,322,165
[45] Mar. 30, 1982

[54] VUV PLASMA ATOMIC EMISSION SPECTROSCOPIC INSTRUMENT AND METHOD

[75] Inventors: Stephen R. Ellebracht, Lake Jackson, Tex.; Charles M. Fairless, Midland, Mich.

[73] Assignee: The Dow Chemical Company, Midland, Mich.

[21] Appl. No.: 14,408

[22] Filed: Feb. 23, 1979

[51] Int. Cl.³ .............................................. G01N 21/73
[52] U.S. Cl. .................................... 356/316; 356/417; 250/372
[58] Field of Search ............... 356/315, 316, 417, 313; 250/372

[56] References Cited

U.S. PATENT DOCUMENTS 4,009,413  2/1977  Elliott et al. ......................... 356/316

FOREIGN PATENT DOCUMENTS 1128625  9/1968  United Kingdom ................ 356/417

OTHER PUBLICATIONS

"Plasma Atomic Emission Spectroscopic Determination of Sulfur" Ellebracht's thesis; pp. 49-55; Aug. 77.
Anal. Chim. Acta 62, 1972, pp. 241-250.
Anal. Chim. Acta 64, 1977, pp. 353-362.
Anal. Chemistry; vol. 44, #14; Dec. 1972, pp. 2379-2382.
"A Controlled-Atmosphere Plasma Arc For Emission Spectrography Of Nonmetal Elements", Heemstra, Applied Spectroscopy, vol. 24, No. 6, 1970, pp. 568-572.
Applied Spectroscopy; vol. 28 #2; 1974; pp. 191-192.

*Primary Examiner*—Vincent P. McGraw

[57] ABSTRACT

A VUV plasma atomic emission apparatus system and method is distinguished by the features of a plasma purge chamber about the plasma generated by the system, a chromator in optical communication and closed gaseous communication with said plasma, preferably through a common port in said plasma purge chamber, purge gas supply means for purging said chromator and ultimately said plasma purge chamber through said common port, vent means preferably operable by draft to continuously exhaust gases from said plasma purge chamber, and focusing means between the plasma and chromator for focusing light from an excited sample introduced into or near said plasma onto said chromator. The continuous gas purging feature establishes a steady state gaseous environment of minimum absorption characteristics to the specific wavelengths of interest, thus expanding the energy band that may be reliably detected (i.e., particularly the difficult 160–200 nanometer band), and which result is accomplished with excellent reproducibility of data and sensitivity.

10 Claims, 6 Drawing Figures

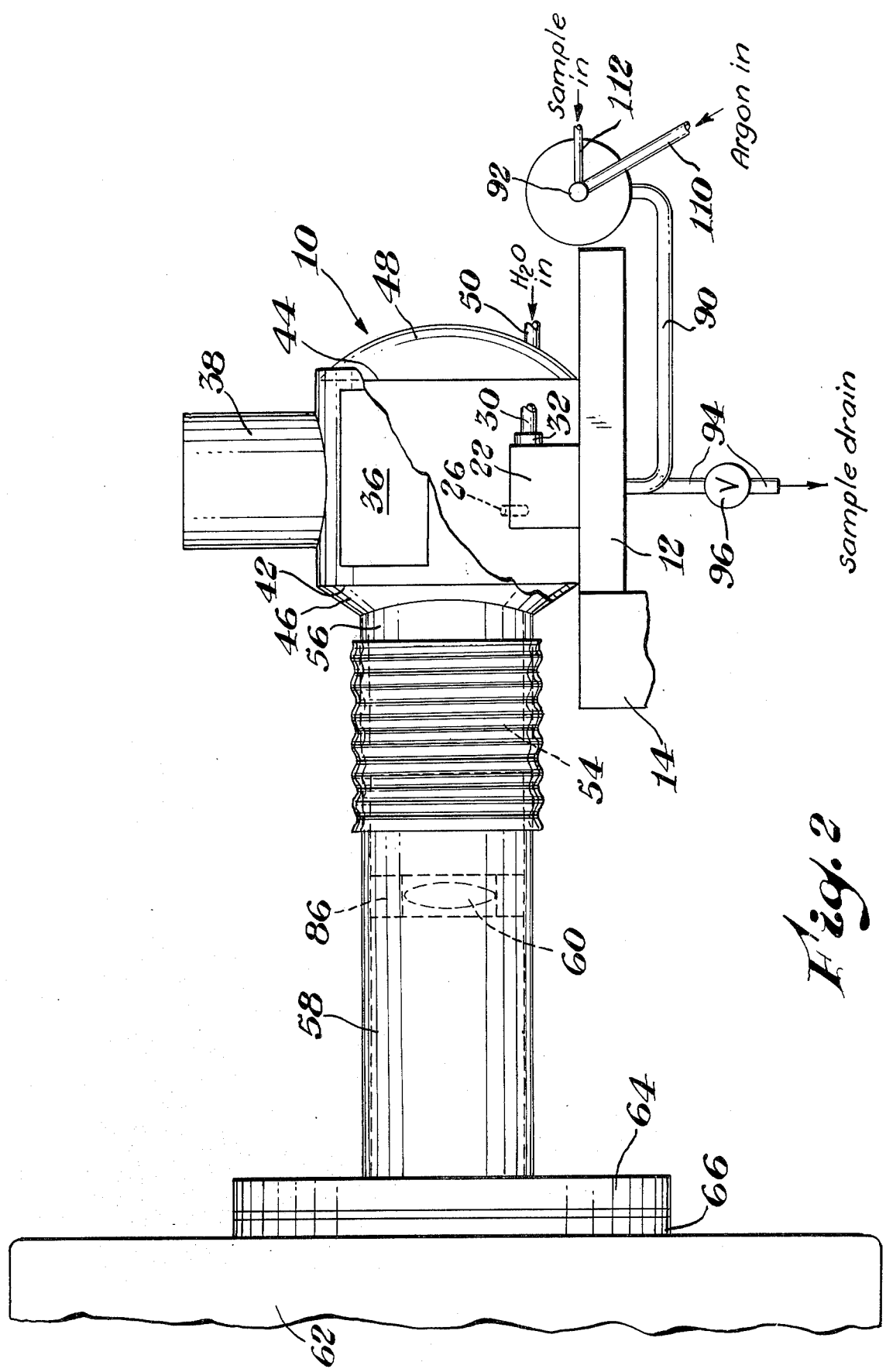

VUV PLASMA ATOMIC EMISSION SPECTROSCOPIC INSTRUMENT AND METHOD

FIELD OF THE INVENTION

The invention relates to the field of elemental analysis wherein sample is atomized and excited by a plasma, and the emitted light analyzed to determine concentration. More particularly, the invention relates to an improved apparatus system and method for accomplishing such analysis in the difficult 160–200 nanometer band.

BACKGROUND OF THE INVENTION

The trace determination of elements having strong emission lines in the sub-200 nanometer wavelength range, by atomic emission spectrometry, poses unique problems because of oxygen absorption phenomena encountered in this region. Ideally, it would be desirable to rid the system of all oxygen in order to achieve optimum levels of sensitivity. Prior work in this area, however, has only minimized rather than satisfactorily solved the problem. Thus, optimum sensitivity levels generally have not been heretofore reliably approached.

In addition, environmental altering of the atmosphere through which the emitted light travels to the detector, unless it produces steady state and repeatable conditions, achieves little in the way of benefit since reproducible data would not be reliably generated. In this vein, even minute variable levels of oxygen in the system can detrimentally influence the data collected. Unless such levels are thus controlled in a simple and expedient manner, i.e., to produce highly steady state conditions repeatable from experiment to experiment, trace analysis may not be feasible, or if feasible, usable only by the most skilled practitioners having utmost familiarity with the quirks of any such given system. Obviously, the latter systems are not quantifiable and thus not in a satisfactory condition for broad implementation.

THE INVENTION

An improved VUV plasma atomic emission apparatus system, having the capabilities sought, and forming the invention hereof, is distinguished by the features of a plasma purge chamber about the plasma generated by the system, a chromator in optical communication and closed gaseous communication with said plasma, preferably through a common port in said plasma purge chamber, purge gas supply means for purging said chromator and ultimately said plasma purge chamber through said common port, vent means preferably operable by draft to continuously exhaust gases from said plasma purge chamber, and focusing means between the plasma and chromator for focusing light from an excited sample introduced into or near said plasma onto said chromator.

A further aspect of the invention involves the improved method of atomic emission spectrometry, wherein for the purposes of elemental analysis, a sample is atomized and excited by a plasma, and the emitted light analyzed to determine concentration wherein the distinguishing steps practiced comprise, confining the plasma within an enclosure, blanketing the plasma with a gas which is substantially non-absorbing of light in the wavelength range of about 160–200 nm, said gas blanket being in a dynamic state by the steps of continuously replenishing same and continuously venting same from the enclosure by draft.

The purging gas used in the invention is preferably argon. Other gases having the preferred characteristic, for exemplary purposes only, include any and all the remaining noble gases, together with nitrogen and/or mixtures of the above. Argon or one of the remaining noble gases, e.g., helium, is similarly preferred for generating the plasma. In certain systems, it is possible to use the same gas, e.g., argon, for generating the plasma and for purging. The instrument of the preferred embodiment and the Example series following shows the feasibility of the latter concept. No observable difficulties with plasma drift or stability were thus encountered, despite the possible logic that a surrounding atmosphere must be distinct from the plasma in order to achieve plasma stability. Nevertheless, plasma stability in cases where drift or poor definition may occur, may be promoted by using a gas distinct in properties such as a nitrogen blanket.

As a general matter, the term chromator as used herein is not to be construed as limited to a specific design, but is intended in scope to cover any device having the functionality of separating and isolating light according to wavelength, and as to any given analysis, light of that wavelength of interest to the analysis.

THE DRAWING

The invention is further disclosed in reference to the preferred embodiment by the following more detailed description, taken in conjunction with the accompanying drawings wherein:

FIG. 2 is a side elevational view of the apparatus of FIG. 1.

DETAILED DESCRIPTION OF THE INVENTION

Figure 1:
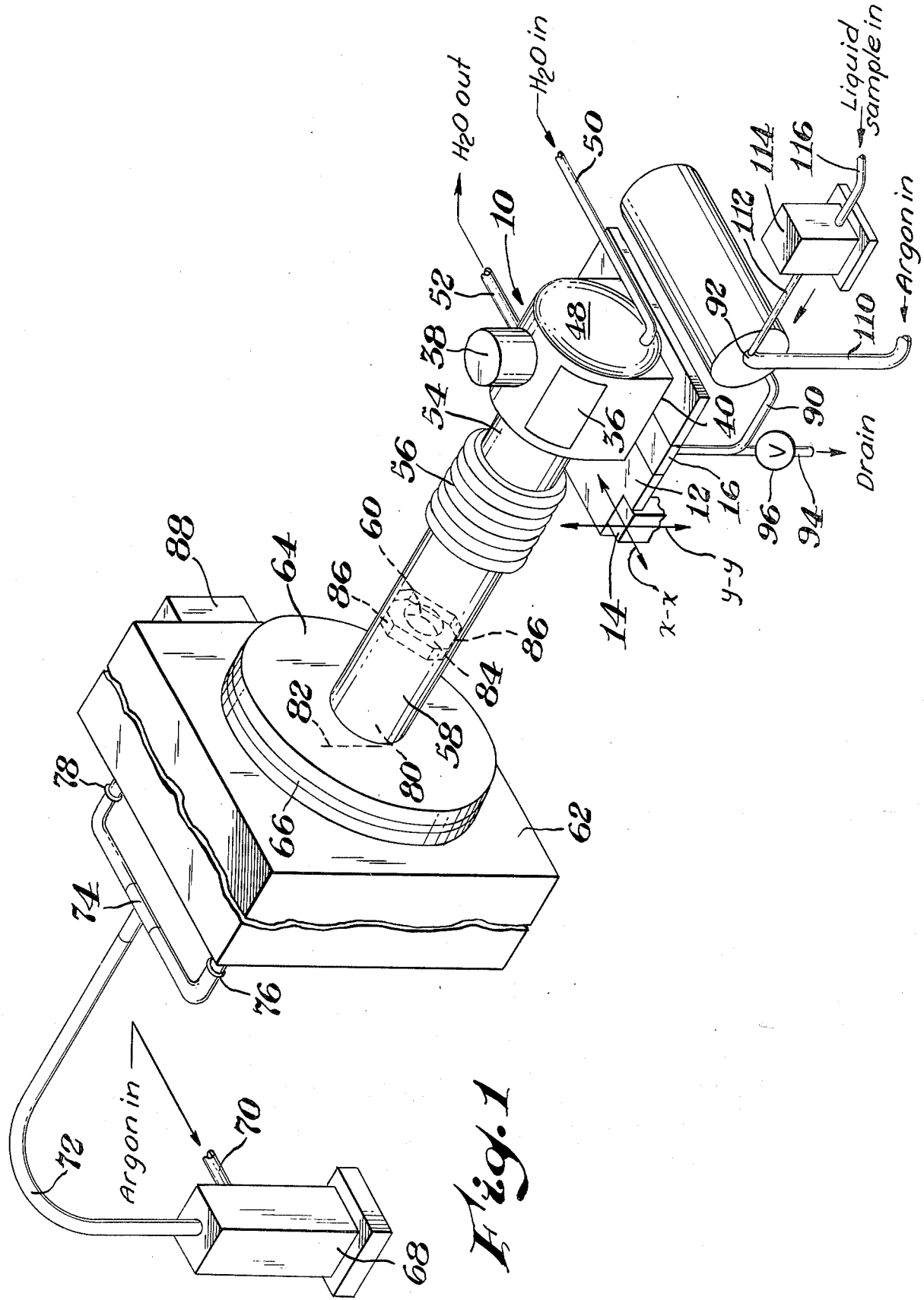
FIG. 1 is an isometric view of a preferred embodiment of a vacuum ultraviolet (VUV) plasma atomic emission spectroscopic instrument constructed using the principles of the present invention.
Figure 4:
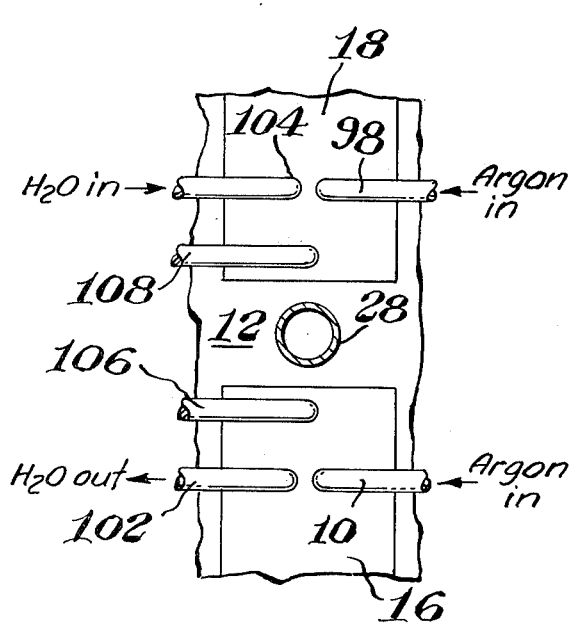
FIG. 4 is a bottom partial view of the purge chamber illustrating the service connections to the plasma source.
Figure 3:
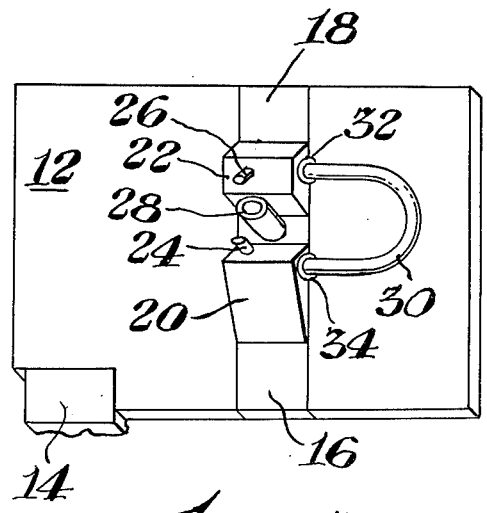
FIG. 3 is an isometric view showing certain of the interior detail of the purge chamber section of the FIG. 1 apparatus.

Referring to the drawing, and most particularly, FIGS. 1 and 2, the VUV plasma atomic emission spectroscopic instrument or apparatus illustrated comprises an enclosed plasma chamber or purge chamber designated generally by reference numeral 10. The plasma purge chamber is seated on a flat base member or base 12 which is mounted for translational movement in the direction of the x—x and y—y axis on a standard optical alignment device shown partially at 14, and preferably, comprising a combination Model 22-4071 and 22-4089 from Ealing Optics. Base 12 preferably comprises a machinable, hardened, high density fiberglas material. Inset in base 12, as shown best in FIG. 3, are a pair of filler blocks 16 and 18, preferably of the same fiberglas material. Attached to the base in the space between the filler blocks are a pair of spaced electrode holders or holder blocks 20 and 22. Mounted in holders 20 and 22, respectively, are ceramic sleeves 24 and 26. Disposed coaxially within the latter are preferably tungsten electrodes (not shown) which cooperate with sleeves 24 and 26 to generate a plasma. The electrodes, in the preferred design, converge together in the known V geometry. Disposed in between the electrodes is a sample introduction means or aerosol chimney 28 (see FIGS. 3 and 4) through which aerosol or gaseous sample is admitted, and dispersed in or near the region of the plasma. The holder blocks 20 and 22 are water cooled, by means of a conduit of flexible tubing 30, preferably of polyvinyl chloride affixed between the blocks by means of brass fittings 32 and 34. The arrangement of the plasma jet or plasma, i.e., elements 20 through 30, are known and described in U.S. Pat. No. 4,009,413, the teachings of which are herein incorporated by reference. Commercial plasma sources made under the teachings of this patent are commercially available from SpectraMetrics, Incorporated, Andover, Mass.

The invention particularly relates to the improvement of the enclosed plasma purge system in which the plasma purge chamber 10, in the design of the preferred embodiment, is seated on base 12, enclosing the plasma source. The chamber is preferably of stainless steel and includes a cobalt viewing glass 36. The geometry is preferentially generally hemispherical to assist smooth gas flow through the system. Centered over the plasma source is a purge vent 38 which operates by draft principles.

Most preferably, the lower lip 40 of the purge chamber is machined to a high degree of smoothness in order to seat flushly with base 12, without requiring physical attachment. Thus, the purge chamber may be conveniently removed for servicing. Alternately, the preferred embodiment contemplates a hingedly attached and thus pivotally removable purge chamber. The middle section of the chamber, i.e., as defined between spaced weld lines 42 and 44 and not critically including vertical side portions 46 and 48, embodies most preferably a double wall construction, thus forming a water cooling jacket through which cooling water is circulated via water inlet hose 50 and outlet hose 52.

The side portion 46 is joined rigidly to a sleeve or hollow light transmitting means 54, such as by welding, the latter being also most preferably of stainless steel. Sleeve 54 defines an internal passage or port means that is aligned with the centerline of the purge chamber (at least one port means is employed, although several may be employed in alternate and satisfactory designs). A flexible tube element, preferably a paper flex tubing 56, is fitted at one end over sleeve 54, and at its other end, over an elongated purge tube or hollow connector or connector element 58 constructed such as transparent Plexiglas, but which alternately, may be coated with black paint to minimize reflection. Preferred tube dimensions are non-critically, 5 cm O.D., 4.4 cm I.D., and 12 cm axial. The flex tube cooperates with translational device 14 for adjusting the optical alignment between the plasma source, a biconvex lens element or light focusing means 60 mounted interiorly of purge tube 58, and a monochromator 62 affixed to the purge tube by a flange coupling 64 and seating gasket 66. The preferred embodiment uses a vacuum operated type, Model 218, McPherson monochromator. Since the model designated is adapted for internal evacuation, it is readily suited to compatibly incorporate the modifications required in practicing the essence of the present invention.

These modifications include the addition of a gas flow meter or regulator 68, (preferably a size 2-4-65A, from Brooks Instrument Division, Emerson Co.) adjustable between flow rates of 1–10 standard cubic feet per hour. An incoming pressurized purge gas line 70 into the gas flow regulator provides pressurized gas, which is outfed through outgoing line 72 to a t-fitting 74. The fitting routes the gas to a pair of spaced inlet ports 76 and 78, of the monochromator, the latter provided in the above-designated commercial device. Ultimately the infeed gas emerges from the forward entrance 80 of the monochromator in communication with purge tube 58. Inside forward entrance 80 is an optical light transmission slit, shown and represented by dotted line 82.

The invention critically requires the introduction into the monochromator of a controlled gaseous environment maintained continuously from the plasma source to a suitable detector, e.g., a photomultiplier tube 88 attached to monochromator 62, and preferably comprising a Model 9783B Photomultiplier tube from EMI Gencom, Inc. To this end lens 60 is mounted in a holder element 84 which is adapted to form passageways 86, for continuous gas flow past the obstruction of the lens. The lens most preferably is 1" in diameter and constructed of Supersil II, from Acton Research, Acton, Mass.

Referring to further details of the instrument, the monochromator is preferably further modified by coating all mirrors and the grating element with a thin coating of $MgF_2$ in order to minimize light absorption in the higher energy region of the spectrum, this fabrication being available from Acton Research. Further, in respect to the preferred detail of base 12, various line connections are brought to and through the bottom of the base to service the plasma source (see also FIG. 4). These include a Tygon tube 90 communicating between a nebulizer 92 (See FIG. 1) and aerosol chimney 28. Tube 90 includes at an intermediate section, connection to a drain tube 94 through a normal open restrictor valve 96. Further service inlets include gas or plasma gas inlets 98 and 100 connected to electrode sleeves 22 and 24, and supplying plasma source gas to the electrodes. In addition, water inlet and outlet lines 102 and 104 are shown for water cooling mounting blocks 20 and 22, and DC electrical connection lines 106 and 108 for energizing the tungsten electrodes.

The nebulizer, in detail, includes further connection to a gas inlet line 110, and a sample inlet line 112, the latter connecting to a peristaltic pump 114, preferably a catalog No. 53202, from Spectrometrics. The peristaltic pump receives sample as, for example, from a beaker (not shown) through a line connection 116, or alternatively from a gas generating or evolving device shown separately in FIG. 5, and described below, with respect to the Example Series II.

OPERATION/DIRECT LIQUID SAMPLE ANALYSIS

Sample in liquid or liquefied form, preferably in water or a known organic solvent system suitable for use in the field of the invention, is advanced by peristaltic pump 114 to nebulizer 92. Argon gas at a controlled flow rate of preferably between about 2–5 standard cubic feet per hour is simultaneously routed to the nebulizer through line connection 110. The nebulizer resultingly mixes the sample with argon, producing a sample aerosol in argon gas that is ultimately introduced between the tungsten electrodes through nebulizer chimney 28. Argon gas through plasma source inlets 98 and 100 is simultaneously supplied through the annular space defined between the electrodes and sleeve elements 22 and 24, the operation of the electrodes being under sufficient energy to produce a hot plasma of ionized argon gas, into which the aerosol sample is dispersed. Preferred flow rate through the sleeve member is controlled within the range of about 2–4 standard cubic feet per hour. Operating temperature of the plasma is estimated at about 6000° C.–10000° C. The plasma is heated sufficiently to cause excitation of the element or elements of interest in the sample. The light emitted by the excitation of the sample is focused by means of lens 60 onto the light transmission slit of the monochromator which resolves the wavelengths of interest for ultimate detection by the photomultiplier tube in the known manner. The photomultiplier tube is preferably used in conjunction with a current amplifier and current to voltage converter to process the light signal and thus allow recording of the results on a strip chart recorder in the known manner. This is then used to generate the data.

The improvement in operation is realized by means and provision of the purge system. In this respect, preferably argon introduced under pressure into the monochromator, via gas flow meter 68 and connections 76 and 78, is routed internally of the monochromator such that the emitted light passes only through the controlled purge atmosphere thus created. The gas exits from the monochromator through purge tube 58, about lens holder 84, and into purge chamber 10. Argon from this source, and all sources in the system, and the sample aerosol is removed by draft through vent 38. It is understood that the purging gas most desirably flows and sweeps continuously through all areas through which the emitted light travels ultimately to detector 88 (including purging of the detector casing). Consequently, a steady state atmosphere is created by which means it is possible to negate the effects of oxygen absorption, in the 160–200 nm band, in a manner which uniquely achieves excellent sensitivity and reproducibility of data.

The invention is further characterized over known prior systems in terms of capabilities as shown in the examples below.

EXAMPLE SERIES I/DIRECT LIQUID SAMPLE ANALYSIS

Using the instrument design of the preferred embodiment, comparative analysis tests are run using established wet chemical methods to determine the relative reproducibility and accuracy of the plasma purge VUV instrument of this invention. In these experiments, the instrument is initially purged with argon for ten minutes before running samples (to rid the system of the effects of oxygen absorption). Samples can then be run in one to two minute intervals. The analysis procedure consists of diluting 34 weight percent $MgCl_2$ one to two, and 68 weight percent $MgCl_2$ one to four by weight in water. The samples are then aspirated directly into an argon plasma. The sulfur emission is recorded as a steady state rise in signal level above background and is measured against sulfur standards prepared in "sulfur-free" 17 percent $MgCl_2$. The experiments of this Example series employ the following instrument settings:

| Monochromator: | |
|---|---|
| Entrance | 25μ |
| Exit | 25μ |
| Wavelength: | 180.7 nm |
| Argon Flow: | |
| Aspirator | 5 SCFH |
| Plasma | 4 SCFH |
| Purge | 3.5 SCFH |
| Sample Aspiration Rate | 2 ml/min |
| PMT Voltage | 800 |

Figure 6:
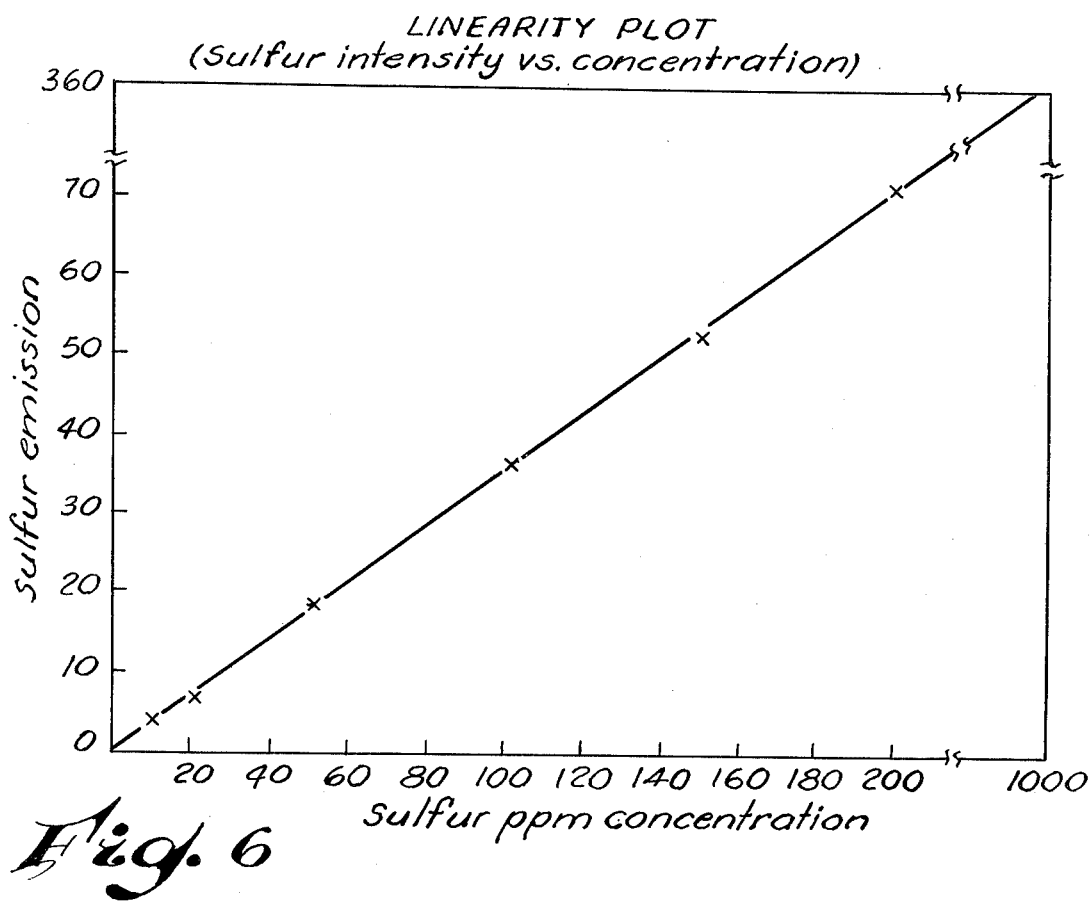
FIG. 6 is a reproduction of a graph generated by practicing the invention, and comprising a calibration curve.

The short-term precision data is shown in Table I. Typically, the precision is within 4 percent relative standard deviation. A calibration curve generated from sulfur made up in 17 percent $MgCl_2$ is shown to be linear up to at least 1000 ppm sulfur (FIG. 6). Accuracy is determined by running ten samples of 34 percent and 68 percent $MgCl_2$ using the described VUV instrument and comparing these results with those previously obtained using reliable wet chemical analytical procedures. More specifically, the analysis is compared with data obtained using the wet chemical methods described by Archer, Analyst, 81, 181 (1956). Although somewhat lengthy, the latter prior art procedure has been routinely used for a number of years and found to be reliable for quantities of sulfur in the 100–300 μg range. The accuracy results are summarized in Table II.

TABLE I

Short-term Precision of the Determination of Sulfate (as Sulfur) in 17 Percent Magnesium Chloride

| *ppm $SO_4^=$ (34% $MgCl_2$) | *ppm $SO_4^=$ (68% $MgCl_2$) |
|---|---|
| 377 | 391 |
| 377 | 400 |
| 389 | 400 |
| 389 | 400 |
| 394 | 391 |
| 377 | 400 |
| 389 | 400 |
| 394 | 400 |
| 377 | 396 |
| 389 | 400 |
| Average 385 | 398 |
| Relative % Std. Deviation 3.8% | 2% |

*The two sets of data represent two different samples.

TABLE II

Accuracy in the Determination of $SO_4^=$ (as Sulfur) in 34% and 68% $MgCl_2$

| Sample Nos. | 34% $MgCl_2$ Wet Chemical ppm $SO_4^=$ | Plasma Purge ppm $SO_4^=$ |
|---|---|---|
| B′ Pl 4/9 | 400 | 390 |
| B600 4/8 | 390 | 380 |
| B600 4/7 | 390 | 394 |
| A600 4/7 | 460 | 457 |
| B600 4/9 | 400 | 396 |
| A600 4/8 | 340 | 352 |
| B′ 600 4/8 | 390 | 384 |
| A′ 600 4/8 | 340 | 354 |
| A′ 600 4/7 | 460 | 449 |
| B 4/9 | 400 | 428 |
| | 68% $MgCl_2$ | |
| 4/4 FBD-2 | 580 | 525 |
| 4/5 CF-B | 398 | 393 |
| 4/10 CF-B | 420 | 405 |

TABLE II-continued

Accuracy in the Determination of
$SO_4^=$ (as Sulfur) in 34% and 68% $MgCl_2$

| | | |
|---|---|---|
| 4/3 CF-B | 390 | 398 |
| 4/8 CF | 360 | 377 |
| 4/8 FBD-2 | 390 | 405 |
| 4/7 CF-B | 400 | 388 |
| 4/9 CF-B | 370 | 388 |
| 4/7 FBD-2 | 520 | 476 |
| 4/8 T-31 | 4590 | 4397 |

The data of Table II illustrates, in these experiments, an accuracy compared with the identified wet chemical procedure of within 4 percent average relative deviation. The data is generated at a rate of about 2 minutes per sample, compared to about 20 minutes per sample for the wet chemical method. The improvement based on the plasma purge is, in addition, ideally suited to determination in the parts per million range of such difficult elements (in addition to sulfur) as phosphorus, arsenic, selenium, mercury, iodine and carbon. More generally, the instrument is ideally suited to analysis of elements having strong atomic emission lines in the region between about 160–200 nanometers, as well as in the more general range above 200 nanometers.

EXAMPLE SERIES II/GAS EVOLUTION

A modified practice of the invention involves the determination of gaseous samples. Most advantageously, this form of the invention is practiced with respect to the analysis of sulfur in sample matrices including high concentration of various salts.

This form of the invention utilizes a sample preparation step necessary to put the sample in solution.

Figure 5:
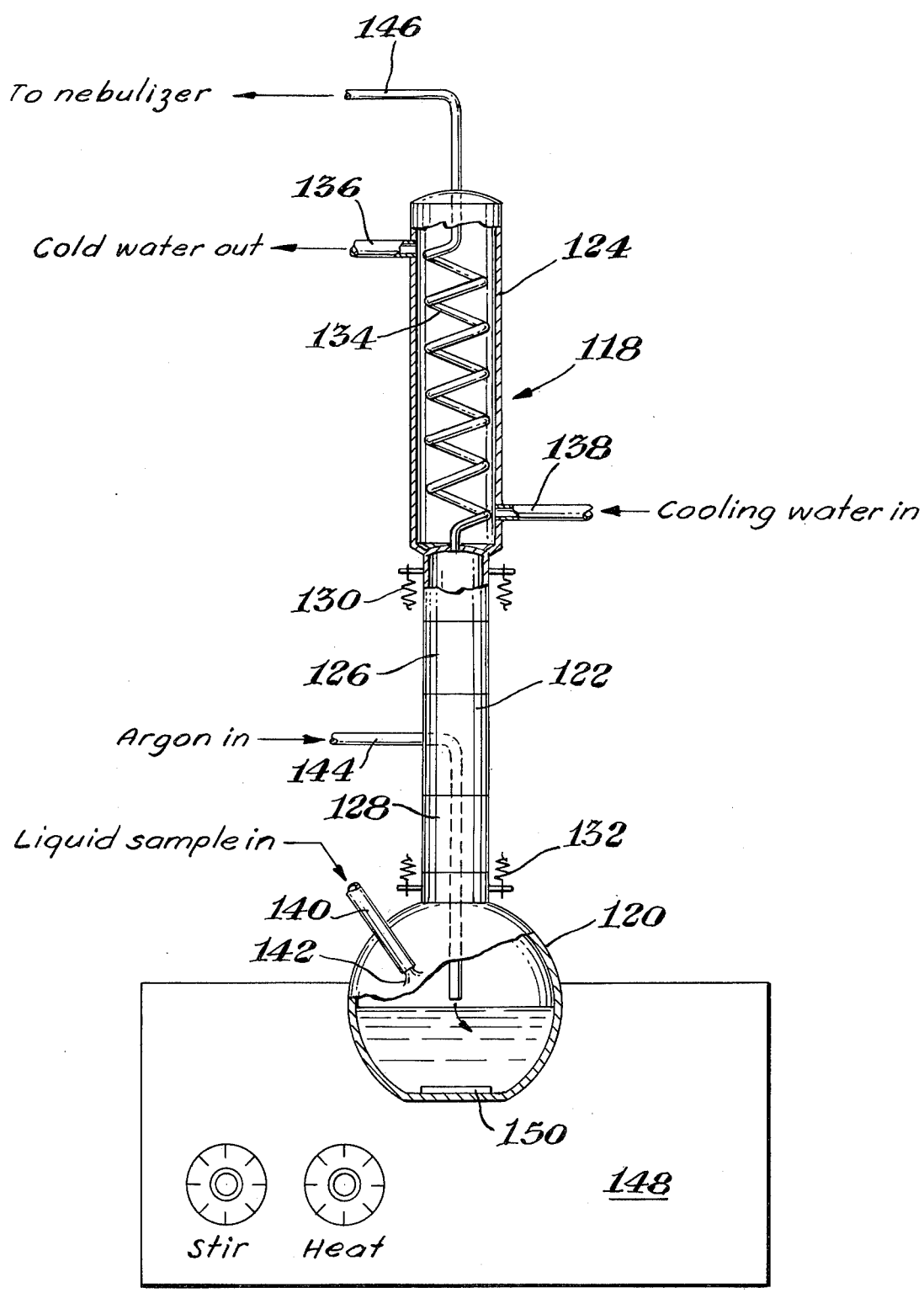
FIG. 5 is a side elevational view showing a modified form of the invention involving gas of the sample to the instrument and preferred apparatus for accomplishing same.

This form of sample analysis according to the invention employs a gas generating or evolution apparatus as shown in FIG. 5, and designated generally by reference numeral 118. Apparatus 118 comprises a flask section 120, a gas inlet adapter section 122, and a condensor section 124. The three sections are joined together by ground glass joints 126 and 128, and held by retaining springs 130 and 132.

A seven-turn spiral condenser 134, cooled by water circulated through water inlet, outlet connections 136, 138 is used to ensure complete condensation of the evolved vapors. A septum support 140 is connected to the boiling flask (250 ml) by means of a ¼" O.D. glass stem 142. The stem is angled so that an injected sample strikes the solution rather than a gas inlet tube designated 144. The heating flask is adapted to be heated and stirred preferably by means of an electrothermal agitator 148 and bar stirrer 150, from Electrothermal Engineering Limited, London, England.

The gas evolution apparatus is connected to VUV instrument by disconnecting the previously described argon line 110 from nebulizer 92, which is then connected to argon inlet 144 of the FIG. 6 apparatus. In conjunction, the evolved sample outlead line, designated 146, is connected to nebulizer 92 in the manner previously occupied by line 110.

A solution ideally used for the reduction of sulfur comprises 30 grams of potassium iodide, 30 ml of hydroiodic acid (55–58 percent by weight), 15 ml of hypophosphorus acid (50–52 percent by weight), and is contained in flask 120.

Using the modification of this Example Series II, the analysis of high salt samples may be advantageously performed with no special sample preparation. In performing such analysis, the flask is heated to boiling temperature. Sample in solution is injected into the flask through septum mount 140. Assuming the described reducing solution and a sulfur-containing sample, the sample upon contacting the hot reducing solution causes the sulfur to be reduced to $H_2S$ gas. The salts are separated and remain in the reducing solution. The evolved gas is swept out by argon through the condenser coil, and into the nebulizer for subsequent analysis according to the technique as described, supra.

The data of this experiment uses the preferred following apparatus parameters.

| | |
|---|---|
| Gas Evolution Apparatus: | |
| Flask Heating Temperature | 100° C. |
| Stirring Rate | 1.050 RPM (with standard 1-inch stirring bar) |
| Argon Flow Rate | 2–4 SCF/Hr |
| VUV Instrument Parameters: | |
| Electrode Current | 7 amperes |
| Slit Widths | 25 μm entrance |
| | 25 μm exit |
| Argon Flow Rates | |
| Plasma Source | 2 SCFH |
| Nebulizer | 4 SCFH |
| Purge | 3 SCFH |
| Analytical Wavelength Setting | 180.7 nm |

Three high salt samples (approximately 20 percent KCl; 20 percent MgCl; 20 percent NaCl; 15 percent CaCl), each with varying sulfur content, are analyzed according to the invention, and the analysis is compared with data obtained using the wet chemical methods described by Archer, Analyst, 81, 181 (1956). The results given in Table III show good agreement between the methods.

TABLE III

| | Accuracy,[a,b] | | |
|---|---|---|---|
| | Sample No. 1 | Sample No. 2 | Sample No. 3 |
| Titrimetric | 93.2 ± 0.5 | 96.7 ± 0.3 | 103.2 ± 1.0 |
| Present Method | 95.3 ± 0.4 | 97.3 ± 0.8 | 105.3 ± 1.0 |

[a]Results given as mean of triplicate determinations.
[b]Results in parts per million.

Repeatability is determined by performing 10 consecutive analyses of a 20 percent w/v solution of salt sample known to contain a small amount of sulfur. Each determination is performed by injecting 100 μl of a 20 μg/ml standard solution, followed by 100 μl of the sample solution. The concentration of sulfur in the salt sample is calculated, and from these results, a relative standard deviation is derived. A relative standard deviation of ±2.1 percent shows that the technique has very good short-term reproducibility. (The results are given in more detail in Table IV.)

TABLE IV

| | Repeatability | | |
|---|---|---|---|
| Analysis | Sample Peak Height[1] | Standard Peak Height[1] | Concentration of Sulfur[2] |
| 1 | 70 | 138 | 50.7 |
| 2 | 72 | 143 | 50.3 |
| 3 | 75 | 148 | 50.7 |
| 4 | 74 | 147 | 50.3 |
| 5 | 71 | 145 | 49.0 |
| 6 | 74 | 150 | 49.3 |
| 7 | 76 | 148 | 51.4 |
| 8 | 81 | 154 | 52.6 |
| 9 | 79 | 153 | 51.6 |

TABLE IV-continued

| Analysis | Repeatability | | Concentration of Sulfur[2] |
|---|---|---|---|
| | Sample Peak Height[1] | Standard Peak Height[1] | |
| 10 | 77 | 152 | 50.7 |
| | | $\overline{X}$ = | 50.6 |
| | | S = | 1.06 |
| | | RSD = | ±2.1% |

[1] Expressed in millimeters.
[2] Concentration in parts per million.

As will be understood by those skilled in the art, the instrumentation and method covered by the invention is delineated from the prior art by the distinctive plasma purge feature. The invention is not limited in the selection of the plasma source, chromator, sample introduction and other assemblies described and used in the preferred embodiment. These are intended only to represent the most preferable selection and combination useful in practicing the inventive plasma purge concept and feature. By way of non-limiting example, the invention may be advantageously combined with other known plasma sources, such as inductively coupled and microwave type plasma sources. Alternate detection forms useful in the practice of the invention include photographic detectors, photodiodes and vidicon based detectors. The sample introduction may similarly be varied such as to employ other nebulization devices, such as ultrasonic nebulizers or single droplet generators. Yet other suitable modes of introducing sample may be by known sample vaporization techniques, generally, and/or direct or indirect hook-up to gas or liquid chromatographic separating systems. Accordingly, it is intended that the invention be limited only in a manner consistent and commensurate with the scope of the claims below.

What is claimed is:

1. Apparatus for atomic emission spectroscopic analysis which comprises a plasma chamber, vent means in the plasma chamber for venting gases therefrom by draft, open port means in the plasma chamber for admitting purging gas to the plasma chamber, means for generating a plasma within the internal zone of the plasma chamber, means for dispersing sample for analysis in or near the internal plasma zone of the plasma chamber, a chromator, the chromator being in optical communication with the internal plasma zone of the plasma chamber and being in gaseous communication therewith through said open port means, and means to continuously admit a controlled flow of purging gas interiorly to the chromator for commonly purging the chromator and plasma chamber.

2. The apparatus of claim 1 comprising a hollow light transmitting means connecting the chromator to the plasma chamber and which communicates with said open port means, and which provides through its interior communication for transmitting light and purging gas between the chromator and open port means of the plasma chamber.

3. The apparatus of claim 2 wherein said hollow light transmitting means contains a light focusing lens nonobstructing to purge gas flow.

4. The apparatus of claim 2 comprising a D.C. plasma generating means.

5. The apparatus of claim 4 comprising a D.C. plasma generating means which employs electrodes positioned in the V-configuration.

6. In the method of elemental analysis wherein sample is atomized and excited by a plasma, and the emitted light analyzed to determine concentration, the steps comprising generating a plasma within a plasma chamber, dispersing a sample in or near the plasma which produces a characterizing light emission in the sub-200 nm wavelength range, transmitting the light to be analyzed to a chromator and detector, purging essentially all void space coincident with the path of travel of the light emission from the plasma to said detector with a purging gas which permits detection of said characterizing light emission, said purging step comprising admitting purging gas at a constant rate to the chromator for flow therefrom ultimately and continuously to the plasma chamber, and continuously venting the purge gas admitted to the chamber by draft.

7. The method of claim 6 wherein the purging and plasma gases commonly comprise argon.

8. The method of claim 6 comprising generating the plasma using a D.C. source with electrodes arranged in the V-configuration.

9. The method of claim 8 wherein the light emission and purging gas are transmitted commonly through an open port means in the plasma chamber.

10. The method of claim 9 wherein the sample emits light for analysis in the wavelength range of about 160–200 nm.

* * * * *